United States Patent
Brannan

(10) Patent No.: US 8,920,410 B2
(45) Date of Patent: Dec. 30, 2014

(54) PERIPHERAL SWITCHING DEVICE FOR MICROWAVE ENERGY PLATFORMS

(75) Inventor: Joseph D. Brannan, Erie, CO (US)

(73) Assignee: Covidien LP, Mansfield, MA (US)

( * ) Notice: Subject to any disclaimer, the term of this patent is extended or adjusted under 35 U.S.C. 154(b) by 392 days.

(21) Appl. No.: 13/464,021

(22) Filed: May 4, 2012

(65) Prior Publication Data

US 2013/0296841 A1 Nov. 7, 2013

(51) Int. Cl.
*A61B 18/04* (2006.01)
(52) U.S. Cl.
USPC .......................................................... 606/33
(58) Field of Classification Search
USPC .......................................................... 606/33
See application file for complete search history.

(56) References Cited

U.S. PATENT DOCUMENTS

| | | |
|---|---|---|
| 4,190,053 A | 2/1980 | Sterzer |
| 4,741,348 A | 5/1988 | Kikuchi et al. |
| 5,344,435 A | 9/1994 | Turner et al. |
| 5,569,245 A | 10/1996 | Guglielmi et al. |
| 5,830,212 A | 11/1998 | Cartmell et al. |
| 6,228,079 B1 | 5/2001 | Koenig |
| 7,553,309 B2 | 6/2009 | Buysse et al. |
| 7,993,338 B2 | 8/2011 | Klimovitch et al. |
| 8,174,267 B2 * | 5/2012 | Brannan et al. ............... 324/415 |
| 2008/0319434 A1 | 12/2008 | Rick et al. |
| 2009/0163907 A1 | 6/2009 | Jarrard et al. |
| 2012/0239025 A1 * | 9/2012 | Smith .............................. 606/34 |

FOREIGN PATENT DOCUMENTS

| | | |
|---|---|---|
| GB | 2 045 620 | 11/1980 |
| JP | 2002-253569 | 9/2002 |

OTHER PUBLICATIONS

Extended European Search Report corresponding to EP 13 18 6409,6, completed Jul. 8, 2013 and mailed Sep. 18, 2013; (11 pp).

* cited by examiner

*Primary Examiner* — George Manuel

(57) ABSTRACT

An electrosurgical system is provided and includes a power source, a microwave applicator, a switching mechanism and a controller. The power source is configured to generate microwave energy. The microwave applicator is configured to deliver microwave energy from the power source to tissue. The switching mechanism includes a housing having input and output ports. The input port is connectable to the power source and the output port is connectable to the microwave applicator. The housing is configured to house one or more switches therein. The controller is in operative communication with the switching mechanism to toggle the switch from a first state, wherein microwave energy generated by the power source is directed to the microwave applicator to a second state, wherein microwave energy is directed to a resistive load operably coupled to the switching mechanism.

15 Claims, 3 Drawing Sheets

PERIPHERAL SWITCHING DEVICE FOR MICROWAVE ENERGY PLATFORMS

BACKGROUND

1. Technical Field

The present disclosure relates to peripheral switching devices and more particularly, to an in-line switching mechanism configured to control power output from a microwave generator to a microwave applicator.

2. Background of Related Art

Electrosurgical systems that utilize microwave generators in conjunction with microwave applicators to treat tissue, e.g., ablate tissue, are well known in the art. Conventional microwave generators are configured to provide microwave energy to the microwave applicator for a specific time frame, e.g., a duty cycle. In certain instances, however, it may prove necessary (or advantageous) to shut the power off prior to the termination of duty cycle. For example, the microwave applicator may need to be moved to a different area on the tissue being treated or to a different location within a patient. Typically, one or more of the "at-the-generator" controls on the microwave generator are activated to terminate or interrupt the duty cycle. In certain instances, for example, to terminate or interrupt the duty cycle, an on/off and/or a reset switch on microwave generator may be pressed. Typically, it is a surgical assistant and not a surgeon that presses these switches. While this approach to control the microwave generator may be effective under some surgical scenarios, hand/foot switching to control the microwave generator may prove advantageous. For example, hand/foot switching capabilities allow a surgeon to directly control the microwave generator, instead having to rely on a surgical assistant.

SUMMARY

In view of the foregoing, an in-line switching mechanism configured to control power output from a microwave generator to a microwave applicator may prove useful in the medical field.

Aspects of the presently disclosed system are described in detail with reference to the drawing figures wherein like reference numerals identify similar or identical elements. As used herein and as is traditional, the term "distal" refers to a portion that is furthest from the user and the term "proximal" refers to a portion of the microwave antenna that is closest to the user. In addition, terms such as "above," "below," "forward," "rearward," etc. refer to the orientation of the figures or the direction of components and are simply used for convenience of description.

An aspect of the present disclosure provides an electrosurgical system that includes a power source, a microwave applicator, a switching mechanism and a controller. The power source is configured to generate microwave energy. The microwave applicator is configured to deliver microwave energy from the power source to tissue. The switching mechanism includes a housing having input and output ports. The input port is connectable to the power source and the output port is connectable to the microwave applicator. The housing is configured to house one or more switches therein. The controller is in operative communication with the switching mechanism to toggle the switch from a first state wherein microwave energy generated by the power source is directed to the microwave applicator to a second state wherein microwave energy is directed to a resistive load operably coupled to the switching mechanism.

The resistive load may be operably disposed within the housing of the switching mechanism and may be in operable communication with the switch.

The switch may be a variable attenuator, a one single pole dual throw switch or the like. In certain instances, the variable attenuator may be an absorptive/reflector pin diode attenuator or a digital programmable step attenuator.

The controller may be a finger-switch that is operably disposed on the microwave applicator. Or, in certain instances, the controller may be a footswitch. In this instance, the switching mechanism may further include a third port that is connectable to the footswitch via a cable.

In certain instances, the switching mechanism may include one or more microprocessors that communicate with the controller for controlling the switch.

In certain instances, the switching mechanism may further include wireless connectivity electronics such that the controller and microprocessor may communicate with one another wirelessly.

The power source may be a microwave generator and the microwave applicator may be a microwave antenna.

Another aspect of the instant disclosure provides an in-line switching mechanism that is configured to provide communication between a microwave generator and a microwave antenna. The in-line switching element includes a housing that has input and output ports. The input port is connectable to the microwave generator and the output port is connectable to the microwave antenna. The housing is configured to house one or more switches and one or more microprocessors therein. The microprocessor is configured to receive an activation signal from a controller in operable communication with the microwave antenna. Upon receiving the activation signal, the microprocessor toggles the at least one switch from a first state wherein microwave energy produced by the microwave generator is directed to the microwave antenna to a second state wherein microwave energy is directed to a resistive load operably coupled to the in-line switching mechanism.

The resistive load may be operably disposed within the housing of the switching mechanism and may be in operable communication with the switch.

The switch may be a variable attenuator, a one single pole dual throw switch or the like. In certain instances, the variable attenuator may be an absorptive/reflector pin diode attenuator or a digital programmable step attenuator.

The controller may be a finger-switch that is operably disposed on the microwave applicator. Or, in certain instances, the controller may be a footswitch. In this instance, the switching mechanism may further include a third port that is connectable to the footswitch via a cable.

In certain instances, the switching mechanism may further include wireless connectivity electronics such that the controller and microprocessor may communicate with one another wirelessly.

Yet another aspect of the instant disclosure provides an electro surgical system that includes a microwave generator, a microwave antenna, a switching mechanism and a controller. The microwave antenna is configured to deliver microwave energy to tissue. The switching mechanism includes a housing having a plurality of ports including a first port connectable to the microwave generator and a second port connectable to the microwave antenna. The housing is configured to house one or more switches, a microprocessor and a power supply therein. The controller is in operative communication with the microprocessor and is configured to provide a command signal to the microprocessor. Upon receiving the command signal, the microprocessor toggles the switch between a first state wherein the switch directs microwave energy to the microwave antenna and a second state wherein the switch directs microwave energy to a resistive load operably coupled to the switching mechanism.

The switch may be a variable attenuator, a one single pole dual throw switch or the like. In certain instances, the variable attenuator may be an absorptive/reflector pin diode attenuator or a digital programmable step attenuator.

The controller may be a finger-switch that is operably disposed on the microwave applicator. Or, in certain instances, the controller may be a footswitch. In this instance, the switching mechanism may further include a third port that is connectable to the footswitch via a cable.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

As noted above, an in-line switching mechanism that is configured to control power output from a microwave generator to a microwave applicator may prove useful in the medical field. To this end, an electrosurgical system utilizing a switching mechanism that is connectable to a power source and a microwave applicator is provided. The switching mechanism includes one or more switches and is in operative communication with a controller to toggle the switch between first and second states. Specifically, in the first state the switch directs microwave energy generated by the power source to the microwave applicator. And, in the second state the switch directs microwave energy to a resistive load operably coupled to the switching mechanism. In accordance with the instant disclosure, a user can directly control microwave energy delivery without having to rely on an assistant to control microwave energy delivery.

Figure 1:
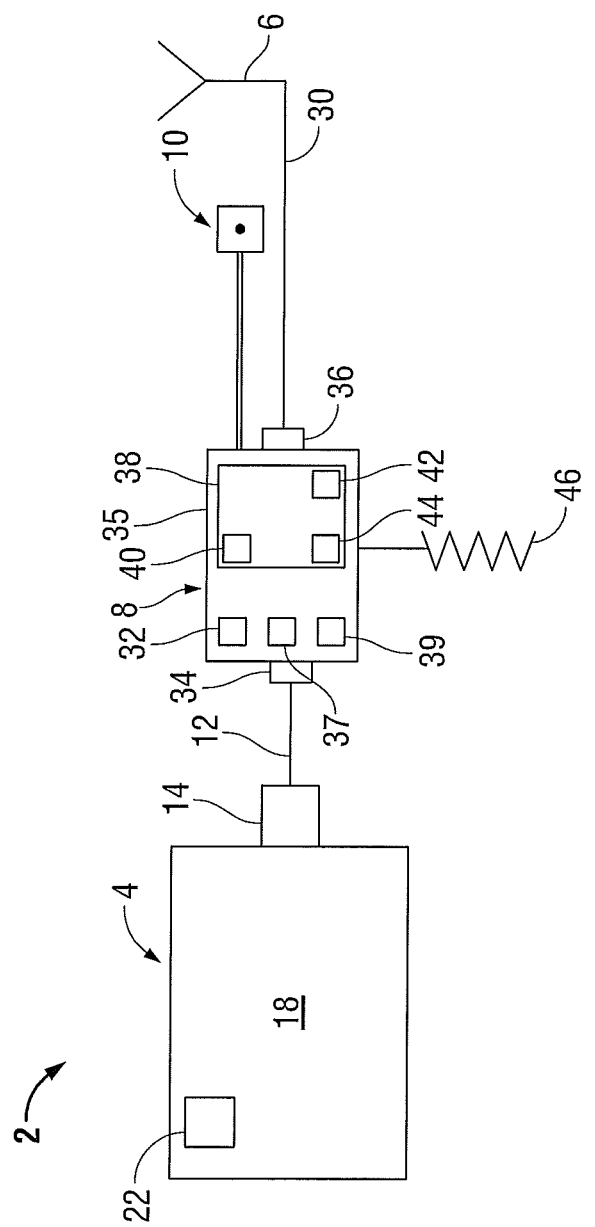
FIG. 1 is a schematic block diagram of a microwave ablation system in accordance with the present disclosure.

FIG. 1 illustrates a schematic block diagram of an electrosurgical system 2 in accordance with an embodiment of the present disclosure. The system 10 includes a power source 4, a microwave applicator 6, a switching mechanism 8 and a controller 10.

Figure 2:
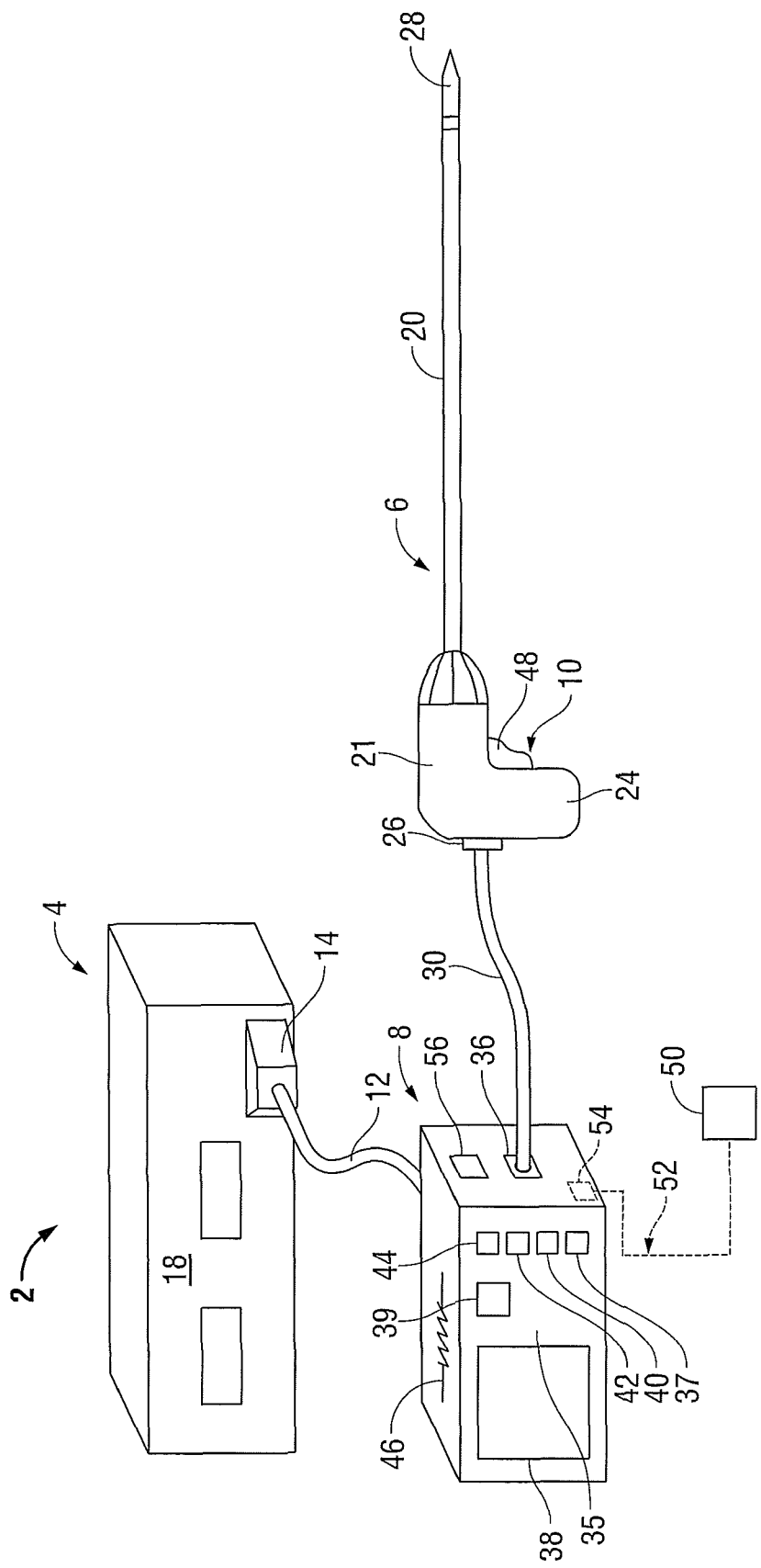
FIG. 2 is a perspective view of the microwave ablation system depicted in FIG. 1.

Power source 4 selectively and removably couples to the switching mechanism 8 via a cable 12 (FIGS. 1 and 2). Cable 12 connects to an output port 14 disposed on the power source 4 and connects to an input port 34 on the switching mechanism 8. Power source 4 is configured to supply electrosurgical energy, e.g., microwave energy, to the microwave applicator 6. In the illustrated embodiment, the power source 4 is a generator 18 and may include a power supply (not explicitly shown) and a microwave output stage (not explicitly shown). In embodiments, generator 18 may also be configured to provide RF energy. The power supply provides DC power to the microwave output stage which then converts the DC power into microwave energy and delivers the microwave energy to the microwave applicator 6 (FIGS. 1 and 2). Generator 18 includes a controller 22 (FIG. 1) that may include analog and/or logic circuitry for processing sensed values provided by one or more modules associated with the generator 18. The controller 22 (or components operably associated therewith) accepts one or more measured signals associated with the microwave applicator 6 when the microwave applicator 6 is radiating energy.

With reference to FIG. 2, microwave applicator 6 includes a housing 21, an elongated shaft 20, a handle 24, and an electrosurgical energy connector 26. Connector 26 is provided at a proximal end of the housing 21 and is configured to connect the microwave applicator 6 to the switching mechanism 8 (FIG. 2). Connector 26 is also configured to supply electrosurgical energy to a conductive tip 28 operably disposed at a distal end of elongated shaft 20 (FIG. 2). In particular, conductive tip 28 and elongated shaft 20 are in electrical communication with connector 26 via an internal coaxial cable (not shown in detail) that extends from a proximal end of the microwave applicator 6 and operatively couples to a radiating section (not shown in detail) operably disposed within the shaft 20 and adjacent the conductive (radiating) tip 28. As is common in the art, the internal coaxial cable may include a dielectric material and an outer conductor that surrounds each of an inner conductor and the dielectric material.

As is conventional in the art, radiating section, by way of conductive tip 28 (or in certain instances without conductive tip 28), is configured to deliver microwave energy to a target tissue site. To this end, elongated conductive tip 28 (and/or shaft 20) may be formed of suitable conductive material including, but not limited to copper, stainless steel or other conductive metals. In certain instances, conductive tip 28 (and/or shaft 20) may be plated with other materials, e.g., gold or silver, to improve certain properties, e.g., to improve conductivity, decrease energy loss, etc. One type of conductive tip that may be utilized with microwave applicator 6 is described in commonly-owned U.S. patent application Ser. No. 12/350,292 filed on Jan. 8, 2009 by Brannan.

Continuing with reference to FIG. 2, housing 21 supports one or more operable components of the microwave applicator 6. In the illustrated embodiment, housing 21 is configured to support the controller 10 (and operable components associated therewith) thereon. In this embodiment, internal circuitry (not shown in detail) associated with the controller 10 is provided in the housing 21 and connects to the switching mechanism 8 via a cable 30 that selectively and releasably couples to connector 26 on the housing 21. One or more leads (not shown) connected to the controller 10 are bundled together with leads of the cable 30 that are configured to provide microwave energy to the radiating section of the microwave applicator 6. The leads of the controller 10 connect to internal circuitry 32 of the switching mechanism 8.

Switching mechanism 8 functions as an in-line switching mechanism and includes a housing 35 that is made from one or more suitable materials, e.g., plastic, metal, ceramic, etc. (FIGS. 1 and 2). Housing 35 includes input and output ports 34 and 36, respectively (see FIGS. 1 and 2). Input port 34 is connectable to input port 14 of the generator 18 via cable 12 and output port 36 is connectable to the microwave applicator 6 via cable 30 that couples to the connector 26 (FIG. 2).

In the illustrated embodiment, housing 35 includes a power supply 37 that is configured to provide power to the internal circuitry of the switching mechanism 8 (FIGS. 1 and 2). Alternately, internal circuitry of the switching mechanism 8 may be energized by the generator 18 (or in certain instances, by the microwave applicator 6).

In embodiments, the housing 35 may be configured to house one or more microprocessors 39 that communicate with the controller 10. Housing 35 may also be configured to house wireless connectivity electronics 56 configured to provide a wireless connection between the controller 10 and microprocessor 39 (and/or the microprocessor 39 and the generator 18) to control one or more functions of the switching mechanism 8, generator 18, and/or microwave applicator 6, as described in greater detail below.

Figure 3A:
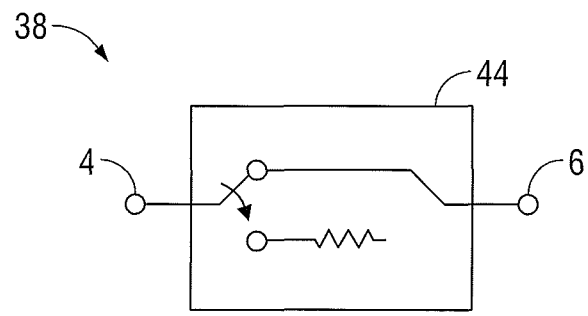
FIGS. 3A-3B are a schematic block diagrams illustrating two types of switching mechanisms that may be utilized with the microwave ablation system depicted in FIGS. 1-2.
Figure 3B:
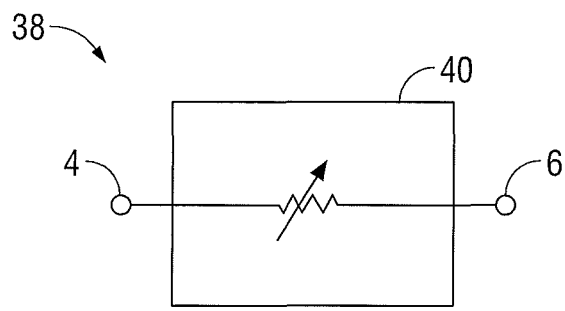

Housing 35 is configured to house one or more switches 38 therein (FIGS. 1 and 2). Switches 38 may be any suitable type of switch. For example, and in the illustrated embodiments, switches 38 can be an electronically variable attenuator. Suitable electronically variable attenuators include, but are not limited to digital programmable step attenuators 40, absorptive/reflective pin diode attenuators 42, and the like (see FIGS. 1-3). Alternately, switch 38 may be a single pole dual throw switch 44 (FIGS. 1 and 2). Regardless of the configuration of switch 38, switch 38 operably couples to a resistive load 46 (FIGS. 1-3).

In the illustrated embodiment, resistive load 46 is provided within the housing 35 and is configured to serve as a "dummy" load. In particular, resistive load 46 is configured to absorb microwave energy that is directed thereto by the switch 38 as a result of the controller 10 providing a control signal to the switch 38.

Controller 10 is in operative communication with the switching mechanism 8 and is configured to toggle the switch 38 from a first state, wherein the switch 38 directs microwave energy from the generator 18 to the microwave applicator 6 to a second state, wherein the switch 38 directs microwave energy to the resistive load 46. To this end, controller 10 may be a finger-switch 48 (FIG. 2) on the microwave applicator 6 (as in the illustrated embodiment) or a footswitch 50 (shown in phantom in FIG. 2). In either instance, the controller 10 communicates a command signal to one of the aforementioned switches 38, e.g., digital programmable step attenuator 40, to toggle the switch 38 between the first and second states.

As illustrated in FIG. 2, finger-switch 48 is supported on the housing 21 of the microwave applicator 6. Finger-switch 48 is depressible by an end user such that upon actuation thereof a command signal is transmitted to one of the aforementioned switches 38 to toggle the switches 38 between the first and second states.

In an embodiment, the footswitch 50 may be configured to function similar to that of the finger-switch 48 and may be utilized to toggle the switch 38 between the first and second states. Unlike the finger-switch 48, however, the footswitch 50 is configured to communicate with the switching mechanism 8 via a cable 52 that is connectable to an optional third port 54 that may be disposed on the housing 35.

While switching mechanism 38 has been described herein as being part of the system 2, it is within the purview of the instant disclosure that the switching mechanism 38 may be configured as a "universal" switching mechanism configured for use with a wide variety of other generators and/or microwave applicators. The specific configuration of controllers 10, however, will depend on the specific configuration of microwave applicator, e.g., a microwave applicator 6 that includes a finger-switch 48 or a microwave applicator that includes a footswitch. In certain embodiments, the footswitch 50 and finger-switch 48 may be utilized in combination with one another.

In use, switching mechanism 38 is coupled to the generator 18 and the microwave applicator 6. For illustrative purposes, it is assumed that the microwave applicator 6 is equipped with a finger-switch 48. Generator 18 is turned on and microwave energy is transmitted to the microwave applicator 6.

In the instance where a surgeon wants to stop transmitting microwave energy to the microwave applicator 6, the surgeon depresses finger-switch 48, which, in turn, transmits a first command signal to one of the aforementioned switches 38. As a result of receiving the command signal, the switch 38 directs microwave energy to the resistive load 46.

Subsequently, the surgeon may depress the finger-switch 48 again, which, in turn transmits a second command signal to the switch 38. As a result of receiving the second command signal, the switch 38 directs microwave energy back to the microwave applicator 6.

System 2 including the switching mechanism 8 overcomes the aforementioned drawbacks associated with conventional electrosurgical systems that utilize microwave generators with at-the-generator controls. In particular, system 2 allows a surgeon to directly control the microwave output to the microwave applicator 6 without the help of a surgical assistant.

From the foregoing and with reference to the various figure drawings, those skilled in the art will appreciate that certain modifications can also be made to the present disclosure without departing from the scope of the same. For example, and as noted above, the housing 35 of the switching mechanism 38 may be configured to house wireless connectivity electronics 56 (FIG. 2). In this instance, the wireless connectivity electronics 56 and microprocessor 39 may be configured provide wireless communication between a surgeon and the switching mechanism 8. Moreover, a transceiver may provide communication between the surgeon and the switching mechanism 8 and may be in the form of a clip (or other suitable device) that attaches to the microwave applicator 6 (or other suitable device or apparel). Alternately, the transceiver may fit in the surgeon's hand, sit on the floor, etc.

In operation, the surgeon simply speaks in a vicinity of the transceiver to toggle the switching mechanism between the first and second states to control microwave energy output to the microwave applicator 6.

In certain instances, the controller 10 may be configured to control other output characteristics of the generator 18, e.g., duty cycle, intensity, etc.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical system, comprising:
a power source configured to generate microwave energy;
a microwave applicator configured to deliver microwave energy from the power source to tissue;
a switching mechanism including a housing having input and output ports, the input port connectable to the power source and the output port connectable to the microwave applicator, the housing configured to house at least one switch therein, wherein the at least one switch is one of an absorptive/reflector pin diode attenuator or a digital programmable step attenuator; and
a controller in operative communication with the switching mechanism to toggle the at least one switch from a first state, wherein the at least one switch directs microwave energy generated by the power source to the microwave applicator to a second state, wherein the at least one switch directs microwave energy to a resistive load operably coupled to the switching mechanism.

2. An electrosurgical system according to claim 1, wherein the resistive load is operably disposed within the housing of the switching mechanism and is in operable communication with the at least one switch.

3. An electrosurgical system according to claim 1, wherein the controller is a finger-switch.

4. An electrosurgical system according to claim 3, wherein the finger-switch is operably disposed on the microwave applicator.

5. An electrosurgical system according to claim 1, wherein the controller is a footswitch and the switching mechanism further includes a third port that is connectable to the footswitch via a cable.

6. An electrosurgical system according to claim 1, wherein the switching mechanism includes at least one microprocessor that communicates with the controller for controlling the at least one switch.

7. An electrosurgical system according to claim 6, wherein the switching mechanism further includes wireless connectivity electronics and wherein the controller and microprocessor communicate with one another via a wireless connection.

8. An electrosurgical system according to claim 1, wherein the power source is a microwave generator and the microwave applicator is a microwave antenna.

9. An in-line switching mechanism configured to provide communication between a microwave generator and a microwave antenna, the in-line switching mechanism comprising:
a housing having input and output ports, the input port connectable to the microwave generator and the output port connectable to the microwave antenna, the housing configured to house at least one switch and at least one microprocessor therein, the at least one microprocessor configured to receive an activation signal from a controller in operable communication with the microwave antenna to toggle the at least one switch from a first state, wherein the at least one switch directs microwave energy produced by the microwave generator to the microwave antenna to a second state, wherein the at least one switch directs microwave energy to a resistive load operably coupled to the in-line switching mechanism, wherein the at least one switch is one of an absorptive/reflector pin diode attenuator or a digital programmable step attenuator.

10. An in-line switching mechanism according to claim 9, wherein the resistive load is operably disposed within the housing and is in operable communication with the at least one switch.

11. An in-line switching mechanism according to claim 9, wherein the controller is a finger-switch operably disposed on the microwave antenna.

12. An in-line switching mechanism according to claim 9, wherein the controller is a footswitch and the in-line switching mechanism further includes a third port that is connectable to the footswitch via a cable.

13. An in-line switching mechanism according to claim 9, wherein the in-line switching mechanism further includes wireless connectivity electronics and wherein the controller and microprocessor communicate with one another via a wireless connection.

14. An electrosurgical system, comprising:
a microwave generator;
a microwave antenna configured to deliver microwave energy to tissue;
a switching mechanism including a housing having a plurality of ports, a first port connectable to the microwave generator and a second port connectable to the microwave antenna, the housing configured to house at least one switch, a microprocessor and a power supply therein, wherein the at least one switch is one of an absorptive/reflector pin diode attenuator or a digital programmable step attenuator; and
a controller in operative communication with the microprocessor and configured to provide a command signal to the microprocessor whereupon receipt of the command signal by the microprocessor, the microprocessor toggles the at least one switch between a first state, wherein the at least one switch directs microwave energy to the microwave antenna and a second state, wherein the at least one switch directs microwave energy to a resistive load operably coupled to the switching mechanism.

15. An electrosurgical system according to claim 14, wherein the controller is one of a finger-switch or a footswitch, wherein the finger-switch is operably disposed on the microwave antenna and, the footswitch connects via a cable to a third port on the housing.

* * * * *